(12) United States Patent
Bosselaers et al.

(10) Patent No.: US 6,174,911 B1
(45) Date of Patent: Jan. 16, 2001

(54) SYNERGISTIC COMPOSITIONS COMPRISING IMAZALIL AND EPOXICONAZOLE

(75) Inventors: Jan Pieter Hendrik Bosselaers, Beerse; Alain Joseph Jean Florimond Garnier, Turnhout, both of (BE)

(73) Assignee: Janssen Pharmaceutica N.V. (BE)

( * ) Notice: Under 35 U.S.C. 154(b), the term of this patent shall be extended for 0 days.

(21) Appl. No.: 09/486,955

(22) PCT Filed: Sep. 1, 1998

(86) PCT No.: PCT/EP98/05711

§ 371 Date: Mar. 3, 2000

§ 102(e) Date: Mar. 3, 2000

(87) PCT Pub. No.: WO99/12422

PCT Pub. Date: Mar. 18, 1999

(30) Foreign Application Priority Data

Sep. 8, 1997  (EP) .................................................. 97202760

(51) Int. Cl.[7] ............................ A01N 43/50; A01N 43/64
(52) U.S. Cl. ............................................ 514/383; 514/399
(58) Field of Search ........................................ 514/383, 399

(56) References Cited

U.S. PATENT DOCUMENTS

| | | | |
|---|---|---|---|
| 3,658,813 | 4/1972 | Godefroi et al. | ................. 260/240 K |
| 5,013,746 | * 5/1991 | Van Gestel | ............................ 514/365 |

FOREIGN PATENT DOCUMENTS

| | | |
|---|---|---|
| 2916853 | 6/1980 | (DE) . |
| 196038B | 10/1986 | (EP) . |
| 0336489 | * 10/1989 | (EP) . |
| 2021951 | 12/1979 | (GB) . |

OTHER PUBLICATIONS

Dialog IP Abstract for EP 196038 (1986).

* cited by examiner

*Primary Examiner*—Allen J. Robinson

(57) ABSTRACT

Synergistic antifungal compositions comprising imazalil, a salt, a stereoisomer or stereoisomeric mixture thereof, and epoxiconazole, a salt, stereoisomer or stereoisomeric mixture thereof, for protecting plants, fruits or seeds. Use of said compositions to protect plants or fruits against fungi.

11 Claims, No Drawings

SYNERGISTIC COMPOSITIONS COMPRISING IMAZALIL AND EPOXICONAZOLE

CROSS REFERENCE TO RELATED APPLICATIONS

This application is the national stage of application Ser. No. PCT/EP98/05711 fled on Sep. 1, 1998, which application claims priority from EP 97202760.1, filed on Sep. 8, 1997.

Synergistic antifungal compositions comprising imazalil, a salt, a stereoisomer or stereoisomeric mixture thereof, and epoxiconazole, a salt, stereoisomer or stereoisomeric mixture thereof, for protecting plants, fruits or seeds. Use of said compositions to protect plants or fruits against fungi.

Various classes of compounds are known as antimicrobial and in particular antifungal compounds. Among these classes, the group of imidazole and triazole derivatives is of particular interest and several of such compounds are now widely used as antimicrobials and in particular as antifungals.

Further, there are known fungicidal combinations comprising two or more such fungicidally active compounds. DE-A-2916853 describes a combination of fenfuran, thiabendazole and imazalil for treating cereal grains. DE-A-2922292 describes combinations of a furan-3-carboxamide, imazalil and/or thiabendazole. DE-A-2823818 describes mixtures of 2,4,5-trimethyl-N-phenyl-3-furancarboxamide with imazalil and/or thiabendazole. And EP-0,336,489, describes synergistic compositions of imazalil and propiconazole.

It now has been found that the compounds imazalil and epoxiconazole act synergistically.

The present invention is concerned with mixtures or compositions comprising imazalil (I), a salt, a stereoisomer or stereoisomeric mixture thereof, and epoxiconazole (II), a salt, a stereoisomer or stereoisomeric mixture thereof, in quantities producing a mutual synergistic antifungal effect, and a carrier.

Imazalil as mentioned hereinabove is the generic name of the compound (±)-1-[2-(2,4-dichlorophenyl)-2-(2-propenyloxy)ethyl]-1H-imidazole, which compound may be represented by the formula

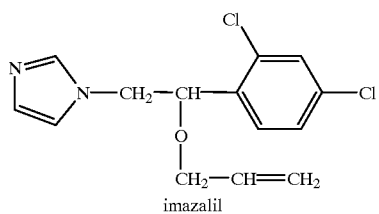
imazalil
(I)

This compound, its synthesis as well as its antifungal properties are described in U.S. Pat. No. 3,658,813.

Epoxiconazole, also known as BAS 480F, is the generic name of the compound cis-(±)-1-[[3-(2-chlorophenyl)-2-(4-fluorophenyl)oxiranyl]methyl]-1H-1,2,4-triazole, which compound may be represented by the formula

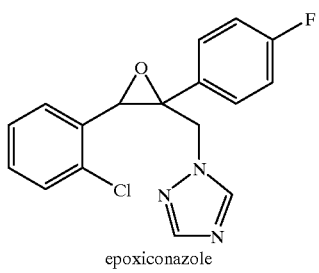
epoxiconazole
(II)

This compound, its synthesis as well as its antifungal properties are described in EP-A-0,196,038.

The active ingredients (I) and (II) for use in the mixtures or compositions according to the present invention may be used as stereochemical mixtures or as pure stereoisomers.

The active ingredients (I) and (II) may be present in base or in salt form, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid, phosphinic acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4methylbenzenesulfonic, cyclohexanesulfamic, 2-hydroxybenzoic, 4-amino-2-hydroxybenzoic and the like acids.

Particular salt forms of imazalil (I) are the sulfate, phosphate, acetate, nitrate or phosphite salts.

The term salt form also comprises metal complexes which the basic components (I) or (II) may form. One of the components may occur as a complex and the other not; or both components may occur as a complex. Metal complexes as mentioned above consist of a complex formed between one or more molecules of the active ingredient and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like. Preferred are the metals pertaining to the transition elements of the fourth period. The metals may be present in each of their possible valences. The metal ions may be present in any of their possible valences, the most preferred metal copper being most advantageously used in its divalent form Cu(II). Suitable copper compounds are copper sulfate, acetate, hydroxide, oxide, borate, fluoride and in particular copper hydroxide carbonate $Cu(OH)_2CuCO_3$. The complexes can be mono- or polynuclear, they may contain one or more parts of the organic molecule as ligands.

The term salt as used hereinabove also comprises the solvates which the-active ingredients of formula (I) and (II)

are able to form. Examples of such solvates are e.g., the hydrates, alcoholates and the like.

The ratio between the active ingredients of formula (I) and (II) may vary within relatively broad ranges and will be dependent on the application aimed at, however said ratio will be so that both active ingredients act synergistically. Particularly, it is contemplated that the compositions of the present invention comprise at least 750 mg/l of (I), and at least 187.5 mg/l of (II). In particular, said compositions comprise (I) in a concentraction between 750 mg/l and 1500 mg/l and (II) in a concentration between 187.5 mg/l and 750 mg/l. Said concentrations of (I) and (II) are taken as their base equivalent.

The quantity of each of the active ingredients in the compositions according to the present invention will be so that a synergistic antifungal effect is obtained. In particular, it is contemplated that in the compositions to be used directly to the plants or the loci thereof, the concentration of imazalil, taken as base equivalent, will be from 750 mg/l to 1500 mg/l; the concentration of epoxiconazole taken as base equivalent is contemplated to be in the range from 187.5 mg/l to 750 mg/l. The active ingredients can be formulated in waxes for use as a cover or coating of e.g. fruits, in particular citrus fruits. Said active ingredients can also be used in all kind of aqueous treatment systems. The said compositions to be used can be obtained from concentrates, such as e.g. emulsifiable concentrates, suspension concentrates, or soluble concentrates, upon dilution with aqueous or organic media, such concentrates being intended to be covered by the term composition as used in the definitions of the present invention.

An emulsifiable concentrate is a liquid, homogeneous formulation of the active ingredients of formula (I) and (II) to be applied as an emulsion after dilution in water. A suspension concentrate is a stable suspension of the active ingredients in a fluid intended for dilution with water before use. A soluble concentrate is a liquid, homogeneous formulation to be applied as a true solution of the active ingredients after dilution in water.

The synergistic mixtures of the present invention are active against a broad range of fungi. As examples of such fungi there may be named Ascomycetes (e.g. *Venturia, Podosphaera, Erysiphe, Monilinia, Uncinula, Aureobasidium, Scierophoma*); Basidiomycetes (e.g. *Hemileia, Rhizoctonia, Puccinia, Coniophora, Serpula, Poria, Uromyces, Gloeophyllum, Lentinus, Coriolus, Irpex*); Fungi imperfecti (e.g. *Botrytis, Helminthosporium, Rhynchosporium, Fusarium, Septoria, Cercospora, Alternaria, Pyricularia, Penicillium, Geotrichum*).

The synergistic mixtures according to the present invention possess advantageous curative, preventive and systemic fungicidal activity to protect plants, in particular culture plants. The present mixtures can be used to protect plants or parts of plants, e.g. fruits, blossoms, flowers, foliage, stems, roots, tubers of plants or culture plants infected, harmed or destroyed by microorganisms, whereby later-growing parts of plants are protected against such microorganisms.

The mixtures according to the present invention show systemic activity. They can further be used in seed disinfection (fruits, tubers, cereal grains) and to treat plant cuttings as well as to combat phytopathogenous fungi occurring in the soil. The mixtures of the present invention are particularly attractive due to their good plant tolerance and-lack of environmental problems (low application rates).

As examples of the wide variety of culture plants in which the combinations of active ingredients according to the present invention can be used, there may be named for example cereals, e.g. wheat, barley, rye, oats, rice, sorghum and the like; beets, e.g. sugar beet and fodder beet; pome and stone fruits and berries, e.g. apples, pears, plums, peaches, almonds, cherries, strawberries, raspberries and blackberres; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes; fibrous plants, e.g. cotton, flax, hemp, jute; citrus fruits, e.g. orange, lemon, grapefruit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugar-cane, tea, vines, hops, bananas, rubber plants, as well as ornamental plants, e.g. flowers, shrubs, deciduous trees and evergreen trees such as conifers. This enumeration of culture plants is given with the purpose of illustrating the invention and not to delimiting it thereto.

The combinations of active ingredients of formulae (I) and (II) are preferably applied as compositions. The active ingredients of formula (I) and those of formula (II) can be applied to the plants or to the loci thereof simultaneously, or can also be administered consecutively within a time period selected so that both active ingredients are allowed to act synergistically, e.g. within 24 hours. In such applications, the active ingredients are used optionally together with adjuvants conventionally employed in the art of formulation such as carriers, surfactants or other useful additives. Therefore, the present invention also concerns products comprising a compound of formula (I), a salt, a stereoisomer or stereoisomeric mixture thereof, and a compound of formula (II), a salt, a stereoisomer or stereoisomeric mixture thereof, as a combination for simultaneous, separate or sequential use in antifungal applications. Such products may consists of a suitable package comprising containers with both active ingredients, preferably in formulated form. Such formulated forms in general have the same composition as described for the formulations containing both active ingredients.

Appropriate carriers and adjuvants for use in the compositions of the present invention may be solid or liquid and correspond to suitable substances known in the art of formulation, such as, for example natural or regenerated mineral substances, solvents, dispersants, surfactants, wetting agents, adhesives, thickeners, binders, fertilizers or anti-freeze agents.

A particular mode of administering an active composition comprising at least one of the active ingredients of formulae (I) and (II), is the administration to the aboveground parts of plants, in particular to the leaves thereof (leaf-application). The number of applications and the administered doses are chosen in accordance with the biological and climatic conditions of life of the causative agent. The active ingredients though, can also be applied to the soil and get into the plants through the root system (systemic activity), in case the locus of the plants is sprayed with a liquid composition or if the compounds are added to the soil in a solid formulation e.g. in the form of a granulate (soil application). The compounds of formulae (I) and (II) can also be coated on seeds, in case the seed grains seed are drenched consecutively with a liquid composition of the active ingredients or if they are coated with a previously combined composition.

The compositions of the present invention are particularly useful in post-harvest treatment of fruits, especially citrus fruits. In the latter instance, the fruits will be sprayed with or dipped or drenched into a liquid formulation or the fruit may be coated with a waxy composition. The latter waxy composition conveniently is prepared by thoroughly mixing a suspension concentrate with a suitable wax. The formulations for spray, dip or drench applications may be prepared upon dilution of a concentrate such as, e.g. an emulsifiable concentrate, a suspension concentrate or a soluble liquid, with an aqueous medium. Such concentrate in most instances consists of the active ingredients, a dispersing or suspending agent (surfactant), a thickening agent, a small amount of organic solvent, a wetting agent, optionally some anti-freeze agent, and water.

The combinations of active ingredients of formulae (I) and (II) may in general be applied as compositions. The active ingredients of formula (I) and those of formula (II) can be applied either simultaneously, or consecutively, to the plants or the loci thereof, optionally in admixture with adjuvants conventionally employed in the art of formulation such as, for example, carriers, surfactants and other additives which may improve the application.

Apart from both the aforementioned active ingredients of formula (I) and (II), the compositions according to the present invention may further comprise other active ingredients, e.g. other microbiocides, in particular fungicides, and also insecticides, acaricides, nematicides, herbicides, plant growth regulators and fertilizers.

The active ingredients of formula (I) and (II) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomizing, dusting, scattering or pouring, are chosen in accordance with the intended objectives and the prevailing circumstances.

The formulations, i.e. the compositions, preparations or mixtures comprising the active ingredients and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable surface-active compounds to be used in the compositions of the present invention are non-ionic, cationic and/or anionic surfactants having good emulsifying, dispersing and wetting properties. The term "surfactants" will also be understood as comprising mixtures of surfactants.

Appropriate carriers and adjuvants for use in the compositions of the present invention may be solid or liquid and correspond to suitable substances known in the art for preparing formulations for treating plants or the loci thereof, or for treating plant products, in particular for treating wood, such as, for example, natural or regenerated mineral substances, solvents, dispersants, surfactants, wetting agents, adhesives, thickeners, binders, fertilizers, anti-freeze agents, repellents, colour additives, corrosion inhibitors, water-repelling agents, siccatives, UV-stabilizers and other active ingredients.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, earth alkaline metal salts or unsubstituted or substituted ammonium salts and contain an alkyl radical having from 8 to 22 carbon atoms said alkyl also comprising radicals derived from acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalene-sulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopoly- propylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxy-ethanols, castor oil polyglycol ethers, polypropylenepolyethylene oxide adducts, tributylphenoxypolyethoxyethanol, polyethylene glycol and octylphenoxypolyethoxy-ethanol. Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$ alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethyl-ammonium chloride or benzyldi(2-chloroethyl) ethylammonium bromide.

The surfactants customarily employed in the art of formulation are described e.g. in the following publications "McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., New York, 1980–81.

Particularly advantageous additives useful to improve the application and reduce the dose of the active ingredients, are the natural (animal or plant) or synthetic phospholipids of the cephalin or lecithin type such as, for example, phosphatidyl-ethanolamine, phosphatidylserine, phosphatidylglycerine, lysolecithin, or cardiolipin. Such phospholipids may be obtained from animal or plant cells, in particular from brain-, heart-or liver tissue, egg yolks or soy beans. Appropriate such phospholipids are for instance, phosphatidylchlorin mixtures. Synthetic phospholipids are for instance, dioctanylphosphatidylchloline and dipalmitoylphosphatidylcholine.

In case of liquid formulations, and particularly of aqueous or alcoholic formulations, it is recommendable to add an appropriate surfactant, either from the anionic, cationic or neutral type. In particular said surfactants will be of the cationic type and more in particular said surfactant is a quaternary ammonium salt or a mixture of quaternary ammonium salts. Such quaternary ammonium surfactants comprise, for example, ammonium salts having four hydrocarbon radicals which may optionally be substituted with halo, phenyl, substituted phenyl or hydroxy; said hydrocarbon radicals in particular being alkyl or alkenyl radicals; they may also be derived from fatty acids or alcohols, e.g. cetyl, lauryl, palmityl, myristyl, oleyl and the like or from the hydrosylates form coconut oil, tallow oil, soy bean oil, or the hydrogenated forms thereof, and the like.

Examples of such quaternary ammonium salts are of the trimethyl alkyl ammonium halide type, e.g. trimethyl decyl ammonium chloride, trimethyl dodecylammonium chloride, trimethyl tallow ammonium chloride, trimethyl oleyl ammonium chloride; or of the dimethyl allyl benzyl ammonium type, e.g. dimethyl decyl benzyl ammonium chloride, dimethyldodecyl benzyl ammonium chloride, dimethyl hexadecylbenzyl ammonium chloride (commonly designated as "cetalkonium chloride"), dimethyl octadecyl benzyl ammonium chloride, dimethyl coco benzyl ammonium chloride, dimethyl tallow benzyl ammonium chloride; and particularly the dimethyl $C_{8-18}$alkyl benzyl ammonium chloride mixture which is commonly known as "benzalkonium chloride"; dimethyl dialkyl ammonium halides, e.g. dimethyl dioctyl ammonium chloride, dimethyl didecyl ammonium chloride, dimethyl didodecyl ammonium chloride, dimethyl dicoco ammonium chloride, dimethyl ditallow ammonium chloride, dimethyl octyl decyl ammonium chloride, dimethyl dodecyl octyl ammonium chloride, dimethyl dihydrogenated tallow ammonium chloride.

As used in the foregoing enumeration of quaternary ammonium salts, the terms "coco", "tallow" and "hydrogenated tallow" designate those hydrocarbon radicals derived from the hydrosylates of coconut oil, tallow oil or hydrogenated tallow oil.

Apart from both the aforementioned active ingredients of formula (I) and (II), the compositions according to the present invention may further comprise other active ingredients, e.g. other microbiocides, in particular fingicides, and also insecticides, acaricides, nematicides, herbicides, plant growth regulators and fertilizers. As antimicrobial agents, which may be used in combination with the active substances there may be considered products of the following classes: phenol derivatives such as 3,5-dichlorophenol, 2,5-dichlorophenol, 3,5-dibromophenol, 2,5-dibromophenol, 2,5-(resp. 3,5)-dichloro-4-bromophenol, 3,4,5-trichlorophenol, chlorinated hydrodiphenylethers such as, for example, 2-hydroxy-3,2'4'-trichlorodiphenylether, phenylphenol, 4chloro-2-phenylphenol, 4chloro-2-benzylphenol, dichlorophene, hexachlorophene; aldehydes such as formaldehyde, glutaraldehyde, salicylaldehyde; alcohols such as phenoxyethanol; antimicrobially active carboxyhic acids and their derivatives; organometallic compounds such as tributyltin compounds; iodine compounds such as iodophores, iodonium compounds; mono-, di- and polyamines such as dodecylamine or 1,10-di(n-heptyl)-1,10-diaminodecane; sulfonium- and phosphonium compounds; mercapto compounds as well as their alkali, earth alkaline and heavy metal salts such as 2-mercaptopyridine-N-oxide and its sodium and zinc salt, 3-mercaptopyridazin-2-oxide, 2-mercaptoquinoxaline-1-oxide, 2-mercaptoquinoxaline-di-N-oxide, as well as the symmetrical disulfides of said mercapto compounds; ureas such as tribromo- or trichlorocarbanilide, dichlorotrifluoromethyl-diphenylurea; tribromosalicylanilide; 2-bromo-2-nitro-1,3-dihydroxypropane; dichlorobenzoxazolon; chlorohexidine; isothia- and benzisothiazolone derivatives.

As insecticidal agents which may be used in the compositions according to the present invention the following classes of products may be considered: insecticides having a natural origin, e.g., nicotine, rotenone, pyrethrum and the like; chlorinated hydrocarbons, e.g., lindane, chlordane, endosulfan and the like; organic phosphor compounds, e.g. azinphos-ethyl, azinphos-methyl, 1-(4chlorphenyl)-4(O-ethyl, S-propyl)phosphoryl-oxypyrazole, chlorpyrifos, coumaphos, demeton, demeton-S-methyl, diazinon, dichlorvos, dimethoate, ethoprophos, etrimfos, fenitrothion, fenthion, beptenophos, parathion, parathionmethyl, phosalone, phoxim, pirimiphos-ethyl, pirimiphos-methyl, profenofos, prothiofos, sulfprofos, triazophos, trichlorphon; carbamates, e.g., aldicarb, bendiocarb, carbaryl, carbofuran, carbosulfan, cloethocarb, 2-(1-methylpropyl) phenylmethylcarbamate, butocarboxime, butoxycarboxime, fenoxycarb, isoprocarb, methomyl, methiocarb, oxamyl, pirimicarb, promecarb, propoxur and thiodicarb; biological insecticides, e.g., products originating from Bacillus thuringiensis; synthetic pyrethroids, e.g., allethrin, alphamethri, bioresmethrin, bifenthrin, cycloprothrin, cyfluthrin, cyhalothrin, cypermethrin, decamethrin, deltamethrin, fenpropathrin, fenfluthrin, fenvalerate, flucythrinate, flumethrin, fluvalinate, halothrin, permethrin, resmethrin and tralomethrin, alpha-cyano-3-phenyl-2-methylbenzyl-2, 2-dimethyl-3-(2-chloro-2-trifluoromethyl-vinyl) cyclopropancarboxylate; organosilicon compounds such as dimethylphenylsilyl-methyl- 3-phenoxybenzylethers e.g. dimethyl(4-ethoxyphenyl)-silylmethyl-3-phenoxybenzylether; or dimethylphenylsilylmethyl-2-phenoxy-6-pyridylmethylethers e.g. dimethyl(9-ethoxy-phenyl)silylmethyl-2-phenoxy-6-pyridylmethylether or [(phenyl)-3-(3-phenoxyphenyl)propyl](dimethyl)silanes e.g. (4-ethoxyphenyl)[3-(4fluoro-3-phenoxyphenyl)propyl] dimethylsilane, silafluofen; nitroimines and nitromethylenes e.g. 1-(6-chloro-3-pyridinylmethyl)-4,5-dihydro-N-nitro-1H-imidazol-2-amine (imidacloprid); benzoylureas e.g. lufenuron, hexaflumuron, flufenoxuron.

In a further aspect of the present invention there is provided a method of combating fungi comprising treating plants or the loci thereof subsequently or simultaneously with a fungicidally effective amount of imazalil, a salt, a stereoisomer or stereoisomeric mixture thereof, and with epoxiconazole, a salt or stereoisomer or stereoisomeric mixture thereof.

The synergistic activity of irizalil and epoxiconazole can be demonstrated in vitro but also in vivo, e.g. on oranges being inoculated with, for example, Geotrichum candidum and being dipped into a suitable liquid formulation containing both active ingredients.

The following examples are intended to illustrate and not to limit the scope of the present invention in all its aspects.

EXAMPLES

A. Biological examples

Example 1

Compounds: imazalil was applied as imazalil sulfate, containing 75% imazalil base. Epoxiconazole was applied as "Opus™", a formulation containing 125 g of active ingredient per liter. Opus™ is commercially available from BASF.

Inoculation: inoculum of Geotrichum candidum was prepared by suspending an aliquot of conidia and/or mycelial fragments in sterile distilled water. Untreated, thoroughly cleaned oranges were used as the experimental subjects. Each fruit was inoculated on 3 sites, distributed equidistantly around the perimeter, by means of a 10 mm diameter cork-borer previously dipped in the inoculum. Two fruits were used for each treatment concentration.

Treatment: four hours after inoculation, fruits were treated by dipping them in the test solution during one minute.

Compound concentrations: each compound was applied at three concentrations, a median concentration, a twofold higher and a twofold lower concentration. In a preliminary experiment, the median concentration for each compound was determined as the concentration at which the compound displayed only partial efficacy. In this way the chances of detecting possible synergy between compounds were optimalised. The following concentrations (in mg/liter) of imazamil and epoxiconazole were combined in all possible ways:

epoxiconazole: 750/375/187.5/0
imazalil: 1500/750/375/0

After treatment, the oranges were kept in the dark in plastic bags at room temperature.

Evaluation: after six and eight days each inoculated site was inspected for both rotting and fungal development. Fungal attack was quantified by measuring the distance, in mm, between the perimeter of the 10 mm diameter inoculation ring and the perimeter of the damaged zone. When no damage was visible outside the inoculation ring, fungal extension was reported as being 0 mm, but the amount of damage inside the ring was noted under "remarks". After each evaluation round, the fungal extension, in mm, for each treatment was calculated as the mean of the six inoculations concerned. Percentage activity, as compared to untreated controls, was calculated for the treatments.

Possible synergy was investigated using Limpel's formula (Richter, D. L., Pestic. Sci. 1987, 19: 309–315):

$$E_C = X + Y - \frac{X \cdot Y}{100}$$

where $E_c$ is the expected additive response, X is the observed percentage control when compound A is applied alone and Y is the observed percentage control when compound B is applied alone. Synergy was considered to occur when the observed effect of a combination of both compounds was greater than the corresponding $E_c$ value.

TABLE 1 epoxiconazole-imazalil experiment on *Geotrichum candidum*

| Imazalil conc. (ppm) | Epoxiconazole conc. (ppm) | Measured activity (%) 6 days | Measured activity (%) 8 days | Calculated activity (%) 6 days | Calculated activity (%) 8 days |
|---|---|---|---|---|---|
| 375 | — | 33.3 | 0.0 | — | — |
| 750 | — | 0.0 | 0.0 | — | — |
| 1500 | — | 72.2 | 47.7 | — | — |
| — | 187.5 | 75.9 | 56.7 | — | — |
| — | 375 | 96.3 | 86.7 | — | — |
| — | 750 | 100.0 | 100.0 | — | — |
| 375 | 187.5 | 14.8 | 0.0 | 84.0 | 56.7 |
| 375 | 375 | 11.1 | 0.0 | 97.5 | 86.7 |
| 375 | 750 | 16.7 | 11.7 | 100.0 | 100.0 |
| 750 | 187.5 | 90.7 | 71.7 | 75.9 | 56.7 |
| 750 | 375 | 96.3 | 100.0 | 96.3 | 86.7 |
| 750 | 750 | 100.0 | 100.0 | 100.0 | 100.0 |
| 1500 | 187.5 | 100.0 | 91.7 | 93.3 | 77.3 |
| 1500 | 375 | 100.0 | 96.7 | 99.0 | 93.0 |
| 1500 | 750 | 100.0 | 100.0 | 100.0 | 100.0 |

Epoxiconazole—imazalil: there is an obvious synergy between the lowest dose of epoxiconazole (187.5 mg/l) and imazalil at 750 and 1500 mg/l. The same doses of imazalil are also, to a limited extent, synergistic with epoxiconazole at 375 mg/l. However, there is a pronounced antagonism between the lowest dose of imazalil (375 mg/l) and all three doses of epoxiconazole applied.

What is claimed is:

1. A composition comprising imazalil (I), a salt, a stereoisomer or stereoisomeric mixture thereof, and epoxiconazole (II), a salt, a stereoisomer or stereoisomeric mixture thereof, in quantities producing a mutual synergistic antifungal effect, and a carrier.

2. A composition according to claim 1 comprising at least 750 mg/l of imazalil and at least 187.5 mg/l of epoxiconazole.

3. A composition according to claim 1 comprising imazalil in a concentraction between 750 mg/l and 1500 mg/l and epoxiconazole in a concentration between 187.5 mg/l and 750 mg/l.

4. A composition according to claim 1 formulated as a concentrate.

5. A composition according to claim 4 wherein the concentrate is an emulsifiable concentrate, a suspension concentrate or a soluble concentrate.

6. A method for protecting plants or the loci thereof against fungi comprising administering to the plants or the loci thereof a synergistically effective amount of a composition as claimed in claim 1.

7. A method for protecting plants or the loci thereof against fungi comprising administering to the plants or the loci thereof a synergistically effective amount of a composition as claimed in claim 2.

8. A method for protecting fruits against fungi comprising administering to the fruit a synergistically effective amount of a composition as claimed in claim 1.

9. A method for protecting fruit against fungi comprising administering to the fruit a synergistically effective amount of a composition as claimed in claim 2.

10. A method for protecting seeds against fungi comprising administering to the seeds a synergistically effective amount of a composition as claimed in claim 1.

11. A method for protecting seeds against fungi comprising administering to the seeds a synergistically effective amount of a composition as claimed in claim 2.

* * * * *